United States Patent [19]
Bridwell et al.

[11] 4,092,367
[45] May 30, 1978

[54] ALKYLATION OF PHENOLS

[75] Inventors: Billy W. Bridwell, Rosenberg, Tex.; Carl E. Johnson, Brookhaven, Miss.

[73] Assignee: Nalco Chemical Co., Oak Brook, Ill.

[21] Appl. No.: 720,178

[22] Filed: Sep. 3, 1976

[51] Int. Cl.² ............................................. C07C 39/06
[52] U.S. Cl. .................................... 568/785; 568/790
[58] Field of Search ........................ 260/624 R, 624 C

[56] References Cited
U.S. PATENT DOCUMENTS

| | | | |
|---|---|---|---|
| 2,147,256 | 2/1939 | Ipatieff | 260/624 C |
| 2,415,069 | 12/1949 | Arvin | 260/624 C |
| 2,560,666 | 7/1951 | Stevens et al. | 260/624 C |
| 2,833,727 | 5/1958 | Mavity | 252/435 |

Primary Examiner—James O. Thomas, Jr.
Assistant Examiner—Werren B. Lone
Attorney, Agent, or Firm—John G. Premo; Robert A. Miller; Barry W. Sufrin

[57] ABSTRACT

A process of preparing an alkylated phenol which is substantially monoalkylated and para oriented which comprises reacting phenol with a $C_4$-$C_9$ olefin and wherein said olefin is utilized in about 5–10% stoichiometric excess. The broad reaction temperature utilized is about 60°–105° C and the time of reaction is at least 30 minutes. The catalyst utilized is anhydrous $H_3PO_4$ which is used in a value of at least 8% based upon the weight of reactant phenol. The preferred products are p-t-amylphenol and p-t-butylphenol, and in the process of preparing these preferred phenols, the olefin may be reacted in 5–8% stoichiometric excess and the reaction temperature utilized may be 95°–115° C. An additional preferred product is p-nonylphenol derived from a branched propylene trimer.

7 Claims, No Drawings

ALKYLATION OF PHENOLS

The present invention deals with the product of alkylated phenols and, in particular, p-t-butylphenol, p-t-amylphenol, and p-nonylphenol, which are useful in making polymers with formaldehyde. The reaction of phenol (unsubstituted) with an olefin is theoretically on a 1:1 stoichiometric basis and the present invention is related to directing the orientation of the entering alkyl group to the para position. It has been found that an acid catalyst phenol alkylation with phosphoric acid is advantageous to the para orientation with the qualification that the catalyst utilized be anhydrous phosphoric acid. It has been further found that the presence of even 2% or greater water in the reaction mix is deleterious to a favorable product ratio towards para orientation of the entering alkyl group on the phenol.

The relative prior art is set out below.

U.S. Pat. No. 2,428,746 Stillson (Gulf Research) — Utilizes tetraphosphoric acid.

U.S. Pat. No. 2,575,457 Mavity (Universal Oil) — Uses various phosphoric acids on a precalcined silicophosphoric acid base.

U.S. Pat. No. 2,589,253 Hervert et al (Universal Oil) — A calcined free acid of phosphorus and a siliceous adsorbent; column 3, line 32, mentions a monohydric phenol.

U.S. Pat. No. 2,833,727 Mavity et al (Universal Oil) — Utilization of polyphosphoric acid which, at column 4, line 47, may be applied to phenols.

U.S. Pat. No. 3,876,710 Saito et al (Hitachi Chemical) — Production of p-t-butylphenol utilizing a silica-alumina catalyst.

None of the above art utilizes anhydrous $H_3PO_4$ which the present invention has found critical. This compound is defined in VanWazer, Phosphorus and Its Compounds, Volume I Chemistry, 1966, page 482, which states that in crystalline form ortho-phosphoric acid is known as the anhydrous acid, $H_3PO_4$ (mp = 42.35° C).

The process for the present alkylation of phenol may be described as reacting phenol with a $C_4$–$C_9$ olefin wherein the olefin is utilized in about 5–10% stoichiometric excess of the 1:1 reactant ratio. Preferably the olefin is a branched chain olefin and preferred species are i-butylene, i-amylene, and a branched chain propylene trimer or nonene. The reaction temperature utilized is about 50°–105° C and in the case of i-butylene and i-amylene may be a narrow range of 95°–105° C. The time of reaction is at least 30 minutes and may run to several hours. The reaction takes place in the presence of a catalyst, which is anhydrous $H_3PO_4$, and is utilized in at least 8% by weight based on the weight of phenol and a preferred range is 8–25% based on the weight of the phenol.

The process as operated above produces a product ratio in favor of para orientation on the phenol for the entering alkyl group and minimizes as a product di-substituted alkyl products. As stated above, utilization of the anhydrous catalyst has been found critical and deviation of even 2% water produces unfavorable product ratios. The advantage is also viewed in the small amount of olefin used in stoichiometric excess in the broad 5–10% range or the narrow 5–8% applicable to i-butylene and i-amylene as reactants.

In the process it has been possible to react phenol to near extinction (less than 1%) with such olefins as i-butylene while producing a favorable ratio of the product p-t-butylphenol with as little o-t-butylphenol and 2,4-di-t-butylphenol as possible.

By comparison with other catalyst systems under similar parameters of use, the present invention compares quite favorably; for example, anhydrous methane sulfonic acid (MSA) promoted the formation of 2,4-di-substituted product as did ferric chloride. Super Filtrol clay also formed too great an amount of di-substituted product before phenol extinction. Phosphoric acid impregnated clay catalyst was not active enough and also gave an unfavorable product ratio. Polyphosphoric acid gave too much di-substitution and left too much unreacted phenol. Eighty-five percent phosphoric acid gave fair results but also gave an unfavorable product ratio. Even when 85% $H_3PO_4$ was dehydrated in the later stages of the reaction, it yielded an unfavorable product ratio even though the residual phenol was less than 1%.

As to solvents, BTX-type solvents, benzene, toluene, or xylene, were practically equivalent, thus the aromatic solvents were better. An oil was unfavorable, giving poor yield and methanol was very unfavorable in that it dissolved the catalyst.

EXAMPLE 1

Tables 1 and 2 illustrate examples of alkylation of phenol with isobutylene and where the catalyst is described as anhydrous $H_3PO_4$, the results are within the scope of the present invention. In addition, as in Table 2, the olefin has been changed from isobutylene to miscellaneous other olefins as described.

EXAMPLE 2

In a closed reactor a charge was placed consisting of 2042 g (21.7M) phenol and 600 g anhydrous phosphoric acid (99.5%) which had been prepared by azeotroping water off 85% phosphoric acid with toluene. Into the reactor was fed 1277 g (22.8M - a 5% excess) of isobutylene at 2.5 – 4.5 cc/minute over an 11-hour period at 95°–100° C. The product was 7 pounds of t-butylphenol and a gas chromatography analysis showed the following:

|  | Wt. Percent |
|---|---|
| Phenol | 1.0 |
| o-t-butylphenol | 1.5 |
| 2,4-di-t-butylphenol | 6.1 |
| p-t-butylphenol | 91.4 |

The results indicate that a favorable para/ortho (mono-substitution) ratio will follow from use of a very dry phosphoric acid catalyst; i.e., anhydrous phosphoric acid.

TABLE 1

ALKYLATION OF PHENOL WITH ISOBUTYLENE

| Run No. | Catalyst | Wt. % Cat. | Temp. ° C. | Olef/ Phenol | Solvent | PRODUCT G.C. ANAL. - WT. % | | | | |
|---|---|---|---|---|---|---|---|---|---|---|
| | | | | | | Phenol | o-t-Bu | 2,4 di- | p-t-Bu | Other |
| 11 | C-85[1] + $P_2O_5$ | 16/6.4 | 95 | 1.5 | Toluene | 0.9 | 13.9 | 17.8 | 67.4 | — |
| 12 | C-85* | 21 | 122 | 1.35 | Toluene | 0 | 7.0 | 9.4 | 83.6 | — |
| 13 | Anh. $H_3PO_4$[2] | 20 | 122 | 1.10 | Toluene | 0.2 | 5.5 | 9.9 | 84.4 | — |

TABLE 1-continued
ALKYLATION OF PHENOL WITH ISOBUTYLENE

| Run No. | Catalyst | Wt. % Cat. | Temp. °C. | Olef/ Phenol | Solvent | PRODUCT G.C. ANAL. - WT. % | | | | |
|---|---|---|---|---|---|---|---|---|---|---|
| | | | | | | Phenol | o-t-Bu | 2,4 di- | p-t-Bu | Other |
| 14 | 20% Anh. H₃PO₄ | 20 | 110 | 1.11 | Toluene | 0.1 | 8.0 | 11.2 | 80.7 | — |
| 15 | Heel** | 20 | 104 | 1.05 | Toluene | 0.5 | 8.3 | 7.5 | 83.7 | — |
| 16 | Heel** | 20 | 112 | 1.07 | Toluene | 0.2 | 7.6 | 9.6 | 82.7 | — |
| 17 | Anh. H₃PO₄ | 17 | 119 | 1.07 | Toluene | 0.1 | 6.9 | 8.4 | 84.6 | — |
| 18 | Anh. H₃PO₄³ | 21 | 101 | 1.05 | — | 1.2 | 4.4 | 7.5 | 86.8 | — |
| 19 | Anh. H₃PO₄³ | 29 | 108 | 1.05 | — | 1.0 | 1.5 | 6.1 | 91.4 | — |
| 20 | Anh. H₃PO₄ | 7.5 | 105 | 1.13 | — | 1.5 | 14.5 | 11.9 | 72.1 | — |
| 21 | Anh. H₃PO₄ | 7.5 | 127 | 1.0 | — | 6.5 | 9.9 | 7.3 | 76.4 | — |
| 22 | Anh. H₃PO₄ | 7.5 | 128 | 1.09 | — | 4.0 | 9.0 | 9.5 | 77.5 | — |
| 23 | Anh. H₃PO₄ | 7.5 | 110 | 1.20 | — | 0 | 11.9 | 16.9 | 71.2 | — |
| 24 | Anh. H₃PO₄ | 21 | 96 | 1.11 | MeOH | 59.2 | 22.2 | 10.6 | 8.1 | — |
| 25 | Anh. H₃PO₄ | 24 | 100 | 1.09 | Toluene | 0 | 7.0 | 7.4 | 85.6 | — |
| 26 | Anh. H₃PO₄ | 21 | 100 | 1.05 | Heptane | Tr | 7.3 | 3.2 | 89.5 | — |
| 27 | Anh. H₃PO₄ | 22 | 104 | 1.05 | Oil 13 | 0.9 | 7.9 | 5.5 | 85.8 | — |
| 28 | Anh. H₃PO₄ | 7.5 | 109 | 1.05 | Oil 13 | 1.9 | 11.1 | 7.7 | 79.3 | — |
| 29 | Anh. H₃PO₄ | 7.5 | 110 | 1.05 | Oil 13 | 1.0 | 8.1 | 8.4 | 82.5 | — |
| 30 | Anh. H₃PO₄ | 21 | 72 | 1.05 | Heptane | 0 | 10.4 | 8.7 | 80.9 | — |
| 31 | Anh. H₃PO₄ | 22 | 128 | 1.05 | Haptane | 1.4 | 4.3 | 6.0 | 88.3 | — |
| 32 | H₃PO₃ | 21 | 108 | 1.05 | — | 11.1 | 28.7 | 31.6 | 25.9 | 2.6 |

Notes:
¹C-85 is commercial grade 85% phosphoric acid.
²Anh. H₃PO₄ is anhydrous H₃PO₄ prepared by azeotroping water from C-85 with suitable solvent.
³These two runs were 30 mole and 23 mole batches prepared in a two-gallon autoclave.
*This run made using liquefied phenol (88%) subsequently stripped of all water.
**In Run 14 the initial catalyst charge was 20% Anh. H₃PO₄; the heel from this run was used in Runs 15 and 16.

TABLE 2
ALKYLATION OF PHENOL WITH MISCELLANEOUS OLEFINS

| Run No. | Max Temp °C. | Olefin | Olef/ Phenol | Catalyst | Wt. % Cat. | Solvent | PRODUCT G.C. ANAL. - AREA % | | | | |
|---|---|---|---|---|---|---|---|---|---|---|---|
| | | | | | | | Phenol | Ortho- | 2,4-di- | para- | Others |
| 41¹ | 115 | Amylene | 1.07 | Anh. H₃PO₄ | 31 | Toluene | 0.5 | 3.1 | — | 96.4 | — |
| 42¹ | 115 | Amylene | 1.08 | " | 42 | Toluene | tr. | 1.7 | 3.9 | 94.4 | — |
| 43 | 157 | Hexene-1 | 2.0 | AMS² | 18 | — | 0.7 | (99.3% mixture) | | | |
| 44 | 160 | Hexylene | 1.33 | Anh. H₃PO₄ | 31 | Toluene | 5.0 | (about 95% mix.) | | | |
| 45 | 145 | Hexylene | 1.95 | " | 27 | — | 5.0 | (about 95% mix.) | | | |
| 46 | 145 | Hexylene | 2.2 | " | 20 | — | 8.0 | (about 95% mix.) | | | |
| (continuation) | | i-Bu | .27 | | 20 | | 0.9 | (about 99% mix.) | | | |
| 47 | 115 | Hexylene | 1.95 | " | 21 | — | 0.5 | (99.5% mixture) | | | |
| 48 | 120 | Hexene-1 | 1.25 | " | 20 | — | 14.8 | (85.2% mixture) | | | |
| 49 | 130 | Hexylene | 3.1 | " | 20 | — | 1.3 | (98.7% mixture) | | | |
| 50 | 130 | Hex/i-Bu. | 0.8/0.6 | " | 21 | — | 0.4 | (99.6% mixture) | | | |
| 51 | 150 | Diisobu. | 1.25 | " | 27 | — | 0.9 | (99.1% mix. after 13 hrs.) | | | |
| 52 | 133 | Diisobu. | 1.2 | " | 22 | — | 0.6 | (99.4% mix. after 22 hrs.) | | | |
| 53 | 134 | Nonene | 1.25 | P.P.³ | 23 | Toluene | 10 | (about 90% mixture) | | | |
| (continuation) | | i-Bu. | 0.25 | (added sequentially) | | | 0.3 | (>99% mixture) | | | |
| 54 | 140 | Nonene | 1.25 | AMS | 6.5 | Toluene | 5.6 | (94.4% mixture) | | | |
| 55 | 160 | Nonene | 1.5 | AMS | 1 | — | 8.0 | (92% mixture) | | | |
| 56 | 145 | Nonene | 1.25 | BF₃-eth. | 6 | Toluene | 10.5 | (89.5% mixture) | | | |
| 57 | 160 | Nonene | 1.25 | p-tol. SO₃H | 5 | Toluene | 9.8 | (90.2% mix. after 21 hrs.) | | | |
| 58 | 133 | Nonene | 1.0 | Anh. H₃PO₄ | 20 | Toluene | 50.3 | (49.7% mixture) | | | |
| 59 | 132 | Nonene | 1.25 | " | 18 | Toluene | 10.1 | (89.9% mixture) | | | |
| 60 | 140 | Non/i-Bu | 0.5/.96 | " | 18 | Toluene | 0.6 | (>99% mixture) | | | |
| 61 | 146 | Nonene | 1.25 | " | 18 | Toluene | 11.0 | (89% mixture) | | | |

Note:
¹These runs were made in a three-drum pilot plant reactor.
²AMS - Anhydrous methane sulfonic acid.
³PP - Polyphosphoric acid (115% H₃PO₄).

We claim:

1. A process of preparing an alkylated phenol which is substantially monoalkylated and para oriented which comprises reacting phenol with a C₄-C₉ mono-unsaturated non-aromatic olefin, said olefin being utilized in about 5-10% stoichiometric excess and wherein the reaction temperature utilized is about 60°-105° C for at least about 30 minutes in the presence of a catalyst consisting of anhydrous H₃PO₄ in the range 8-25% anhydrous H₃PO₄ by weight based on the weight of phenol and producing a C₄-C₉ alkylated phenol in a favorable product ratio which is substantially para oriented.

2. The process according to claim 1 wherein the alkylated phenol is p-t-butylphenol and the C₄-C₉ olefin is i-butylene.

3. The process according to claim 1 wherein the alkylated phenol is p-t-amylphenol and the C₄-C₉ olefin is i-amylene.

4. The process according to claim 1 wherein the alkylated phenol is p-nonylphenol and the C₄-C₉ olefin is nonene which is a propylene trimer.

5. A process of preparing an alkylated phenol which is substantially monoalkylated and para oriented wherein the phenol is reacted with an olefin selected from the group consisting of i-butylene and i-amylene wherein said olefin is reacted in 5-8% stoichiometric excess and wherein the reaction temperature utilized is about 95°-115° C for at least 30 minutes in the presence of a catalyst consisting of anhydrous H₃PO₄ in the range 8-25% anhydrous H₃PO₄ by weight based on the weight of phenol and producing an alkylated phenol in a favorable product ratio.

6. The process according to claim 5 wherein i-butylene is utilized as the olefin in the reaction and t-butylphenol is produced.

7. The process according to claim 5 wherein i-amylene is utilized as the olefin in the reaction and p-t-amylphenol is produced.